(12) United States Patent
Wuske et al.

(10) Patent No.: US 6,375,896 B1
(45) Date of Patent: Apr. 23, 2002

(54) SWAB ANALYZER FOR THE IMMUNOCHEMICAL DETECTION OF SUBSTANCES

(75) Inventors: Thomas Wuske, Malente; Rainer Polzius, Lübeck; Jessica Mahn, Stockelsdorf; Maria Cerqueira da Costa, Lübeck, all of (DE)

(73) Assignee: Dräger Sicherheitstechnik GmbH (DE)

( * ) Notice: Subject to any disclaimer, the term of this patent is extended or adjusted under 35 U.S.C. 154(b) by 0 days.

(21) Appl. No.: 09/350,077

(22) Filed: Jul. 8, 1999

(30) Foreign Application Priority Data

Mar. 6, 1999 (DE) .......................................... 199 09 891

(51) Int. Cl.$^7$ .............................................. G01N 21/00
(52) U.S. Cl. .............................. 422/58; 422/50; 422/55; 422/56; 422/61; 422/68.1; 422/99; 436/164; 436/169; 436/177; 436/178
(58) Field of Search .............................. 422/50, 55, 56, 422/58, 61, 68.1, 99, 101; 436/518, 528, 531, 535, 44, 177, 164, 169, 178

(56) References Cited

U.S. PATENT DOCUMENTS

| | | | | |
|---|---|---|---|---|
| 5,431,880 A | * | 7/1995 | Kramer | 422/56 |
| 5,622,871 A | * | 4/1997 | May et al. | 436/514 |
| 5,817,522 A | * | 10/1998 | Goodman et al. | 436/165 |
| 5,939,331 A | * | 8/1999 | Burd et al. | 436/518 |
| 6,027,943 A | * | 2/2000 | Kang et al. | 436/518 |
| 6,046,058 A | * | 4/2000 | Sun | 436/514 |
| 6,129,894 A | * | 10/2000 | Rabenecker et al. | 422/61 |
| 6,214,291 B1 | * | 4/2001 | Kerman | 422/61 |

* cited by examiner

Primary Examiner—Jill Warden
Assistant Examiner—Dwayne K Handy
(74) Attorney, Agent, or Firm—McGlew and Tuttle, P.C.

(57) ABSTRACT

A swab analyzer with advantageous handling and detection sensitivity for the immunochemical detection of substances. The analyzer has a housing, an eluent application zone (a swabbing pen 2) and a reaction zone (6). The housing (1) has a local elevation with a central opening, from which a sampling and eluent application zone, designed as a porous swabbing pen (2), projects. The local elevation is provided with an at least partially circular collection groove (3) for receiving excess eluent. A window (10) is present in the housing (1) at a spaced location from the local elevation for evaluating the reaction zone (6) placed under it. The sampling and eluent application zone as well as the reaction zone (6) with the signal zones (7) are in capillary fluid connection with one another.

26 Claims, 2 Drawing Sheets

SWAB ANALYZER FOR THE IMMUNOCHEMICAL DETECTION OF SUBSTANCES

FIELD OF THE INVENTION

The present invention pertains to a swab analyzer for the immunochemical detection of substances with a housing, an eluent application zone and a reaction zone with a signal zone.

BACKGROUND OF THE INVENTION

A process for detecting the contamination of a surface with an analyte by swabbing the analyte from the surface with a swabbing surface that is separate from a test strip, contacting the swabbing surface and the test strip, and subsequently applying an eluent with a subsequent immunological binding reaction, has become known from DE 44 39 429 C2. One drawback of this prior-art process and of the corresponding device is, on the one hand, that a separate swabbing surface must be present for the sampling and, on the other hand, that to contact the swabbing surface and the test strip by means of a special housing for receiving the test strip and the swabbing surface, the swabbing surface must be in contact with the test strip with a minimum pressure, but without preventing or hindering the capillary flow of liquid in the test strip.

SUMMARY AND OBJECTS OF THE INVENTION

Thus, the primary object of the present invention is to provide a swab analyzer of the type described in the introduction, which has a simple design, makes possible improved handling with good sensitivity of detection and has no separate swabbing surface for contacting with a test strip as according to the state of the art.

According to the invention, a swab analyzer is provided for the immunochemical detection of substances. The analyzer includes a housing, an eluent application zone and a reaction zone with signal zone. The housing has a local elevation with a central opening, from which a sampling and eluent application zone designed as a porous swabbing pen projects. The local elevation is provided with an at least partially circular collection groove for receiving excess eluent. A window is present in the housing at a spaced location from the local elevation for evaluating the reaction zone placed under it. The sampling and eluent application zone as well as the reaction zone with the signal zones are in capillary fluid connection with one another.

One essential advantage of the swab analyzer according to the present invention is the reliable, facilitated handling and the selective sensitivity of detection due to the selected porosity and the material of the combined sampling and eluent application zone designed as a swabbing pen. The combined sampling and eluent application zone (swabbing pen) is integrated with the analytical system in one housing.

The local elevation may be conical.

The collection grooves running around the local elevation may be concentric.

The porous surface of the swabbing pen projecting outward from the housing may be rounded. The pore size of the swabbing pen preferably ranges from 10 $\mu$m to 100 $\mu$m. The swabbing pen may consist of a sintered or foamed plastic, especially sintered polyethylene.

The housing can be opened and may consist of a plastic, especially polypropylene.

Using the present invention, substances located on surfaces can be collected and analyzed by manual swabbing with the sampling and eluent application zone designed as a porous swabbing pen. The dropwise application of a specific eluent to the sampling and eluent application zone elutes the analyte present in or on the collected substance into the reaction zone by capillary transport.

There is a need for analyzing substances located on surfaces in both forensic chemistry, environmental analysis and the medical diagnosis of secretions, such as sweat and saliva.

Proteins (allergens) adsorbed on very fine dust particles have been known to cause undesired allergic reactions in sensitized subjects. The pathogenic action of the allergens is concentration-dependent. Specific limit values have been specified, e.g., for mite and cat allergens in house dust. Checking these limit values of the concentrations within the framework of the probing of the exposure potential requires the collection of the very fine dust on a great variety of surfaces, such as mattresses, carpets, upholstered furniture, etc.

In addition, sampling from body fluids, such as sweat and saliva may be provided for establishing the genetic fingerprint. In addition, tests are performed, e.g., from immunological components (such as secretory antibodies) or pharmacological active ingredients in saliva and or sweat. It is common practice in these cases to take swab samples from the skin or from the pharyngeal cavity, which are usually evaluated in a separate analytical procedure.

Thus, the device according to the present invention is used for detection procedures in which the sampling by means of swabbing on surfaces is an integral or associated component of a subsequent analytical procedure with optically perceptible display for a measured concentration of a certain analyte.

The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

DESCRIPTION OF THE PREFERRED EMBODIMENTS

Figure 2:
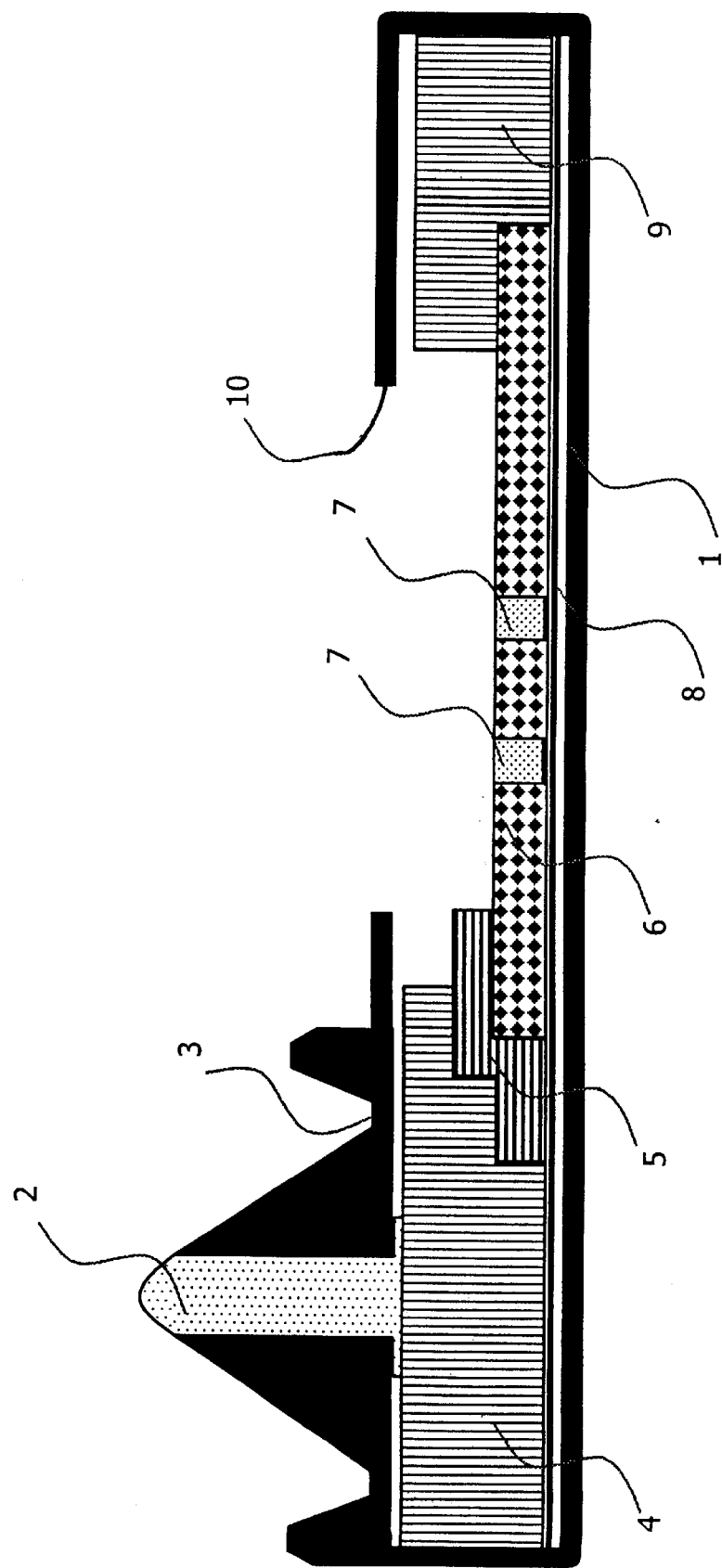
FIG. 2 is a longitudinal sectional view taken through the housing according to FIG. 1.

Referring to the drawings in particular, a housing 1 accommodates all components of the swab analyzer according to the present invention and preferably consists of a plastic, e.g., polypropylene. The housing 1 can be opened and has a window 10, so that both the sampling and eluent application zone designed in the form of a porous swabbing pen 2 and the other analytical elements, which are in fluid connection therewith, including the reaction zone 6, which is visible from the outside, with two signal zones 7 shown as an example, can be replaced as needed. The evaluation of the signal zones 7 is carried out through the window 10 in the housing 1. The sampling and eluent application zone designed as a porous swabbing pen 2 is shown in FIG. 2 as a centrally projecting, conically elevated area of the housing 1 and is provided with a circular collection groove 3 for elution liquid at the low end of the elevation.

The geometric arrangement of the swabbing pen 2 in the area between 45° and 90° relative to the angle to the housing 1 makes possible a specific and efficient sampling from a sampling site. The cylindrical swabbing pen 2 used is preferably rounded on its swabbing side in order to minimize the abrasion of the sample substrate and the abrasion of the swabbing pen 2 proper at the same time. On the underside facing the housing 1, the swabbing pen 2 is flattened and is thus in direct contact with the transfer zone 4. The preferred design of the swabbing pen 2 as a porous plastic combines the advantageous material properties elasticity and rigidity in favor of a low-abrasion swabbing process even on rough surfaces. The suitable materials are preferably all types of sintered or foamed plastics, e.g., polyethylene. In addition, porous glass or metal bodies are also suitable for special requirements of swabbing on soft surfaces. The pore size of the material may range from 10 to 100 $\mu$m. The pores formed by a sintering process or a foaming process make possible the uptake of both liquid and particulate substances. These penetrate into the pores during the swabbing process; the addition of surface-active chemicals (detergents) makes it possible to adapt the hydrophilic or lipophilic character of the porous swabbing pen 2 to the polarity of the sample. The penetration behavior of a liquid substance can be influenced in a specific manner in the best case in favor of a more rapid uptake of an analyte being sought by chemically setting the swabbing pen 2. The selected porosity of the swabbing pen 2 will ultimately also determine the selection of a certain particle fraction.

Figure 1:
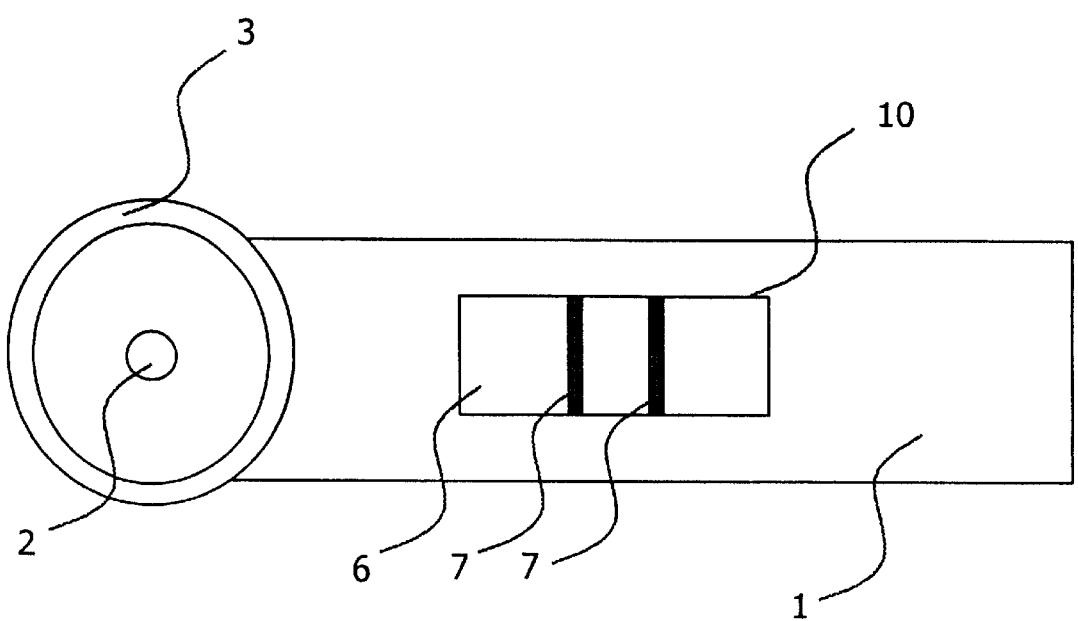
FIG. 1 is a top view of a housing of one exemplary embodiment of the invention.

The amount of substance taken up depends, in general, on the selected porosity of the swabbing pen 2, the integral of the available amount of substance and the surface area swabbed per unit of time, as well as the contact pressure on the surface to be swabbed. In the case of liquid substrates, the uptake of substance can be regulated primarily by varying the contact time with the substrate and the pore volume, the contact pressure not being significant. Subsequent to the sampling with the integrated swabbing pen 2 of the swab analyzer, the elution of the analyte, which is located on the surface of the swabbing pen 2 as a consequence of the sampling or has penetrated into the pores, is performed. To do so, the flat swab analyzer (the dimensions of the housing 1 in the exemplary embodiment according to FIG. 1 are approximately: length 9 cm, maximum width 2 cm, and maximum height 1 cm) must be placed on a support. The swabbing pen 2 is now directed vertically. The elution process takes place within the pores of the swabbing pen 2 after an eluent has been applied dropwise to the surface of the swabbing pen 2. This procedure may be carried out preferably by hand by applying drops from a dropper. The analyte being sought dissolves in the eluent and ultimately reaches the analytical elements in the dilute and sufficiently mobile form. In the case of the uptake of particulate substances, the swabbing pen 2 additionally acts as a filter by the accumulated particles being retained essentially on the surface of the swabbing pen 2. A hydrostatic pressure, which facilitates the capillary transport to the adjoining analytical elements, builds up corresponding to the height of the swabbing pen 2 due to the exposed position of the swabbing pen 2 at an angle to the housing 1. The analyte is preferably transported by the capillary forces of the fine pores of all components of the analytical system (4, 5, 6, 7, 9). The height of the swabbing pen 2 is selected corresponding to the compromise between the need to have the possibility of carrying out a specific sampling and the intent to keep the dilution of the analyte being sought as low as possible in order not to jeopardize the sensitivity of the analytical process.

The mounting of the swabbing pen 2 in the housing 1 also has a collection groove 3. It is thus ensured that droplets of the eluent, which are not absorbed by the swabbing pen 2 immediately, will be retained in the collection groove 3 via a runoff cone of the housing 1 to prevent them from reaching the analytical elements themselves or the sampled surface.

An overflow protection in the form of a recess for excess liquid, not shown in the figures, is integrated in the interior of the housing 1 at the interface between the swabbing pen 2 and the porous transfer zone 4 for the case of an accidental overdosage of the eluent.

The capillary porous analysis system (4, 5, 6, 7, 9) as an integral part of a swab analyzer is characterized by the property of autonomously transporting a liquid to be analyzed. The liquid to be analyzed is taken over directly from the swab compartment via the interface in the form of mutually contacting surfaces of the swabbing pen 2 and the porous transfer zone 4. Due to the suction effect of all components of the analytical system, the liquid analyte reaches a likewise porous collection zone 9 via the conjugate zone 5, the reaction zone 6 and the signal zones 7. Auxiliary agents for visualizing an analyte-specific detection, which agents make possible analyte-specific chemical or biochemical interactions with other, stationary auxiliary agents and with the analyte already due to the fluid transport into the reaction zone 6 and into the signal zones 7 as well as in these zones themselves, are solubilized in the conjugate zone 5 during the flow of the analyte through the different zones of the analytical system. Additional auxiliary agents, which make it possible to visualize an analyte-specific detection, are immobilized in the signal zones 7. All types of biochemical detector structures, e.g., antibodies, receptors, DNA or RNA structures, may be considered for use as auxiliary agents for the analysis. Other analytical auxiliary agents are signal-inducing components, e.g., dyes, stained particles, enzymes, redox and pH indicators.

An especially preferred embodiment of the swab analyzer according to the present invention is the combination of the above-described swab compartment with an immunochromatographic test strip. The connection of the two units in an independent instrument is brought about by an accurately fitting embedding in a housing 1 made of polypropylene, which can be taken apart. The swabbing pen 2, consisting of sintered plastic, which is in turn integrated within the swab compartment with a recess for excess eluent, projects from the housing 1. The housing 1 also has a window 10 as a signal window over the signal zones 7 of the test strip. The analytical result, in the form of bands visible in color, can be read visually through this signal window. A swab analysis preferably takes place as follows:

The swab sample is taken from the object to be analyzed by a swabbing movement of limited duration. This is followed by the elution of the analyte by the specific application of a few drops of an eluent to the swabbing pen 2. Drops pearling off from the swabbing pen 2 subsequently run into the collection groove 3. A portion of the eluent that is essential for the analysis is taken up by the swabbing pen 2. The eluent passes through the swabbing pen 2 and extracts a portion of the analyte taken up on the sample at the same time. Due to capillary transport, the dissolved analyte now reaches the test strip, where an analyte-specific detection reaction takes place.

EXAMPLE 1

Detection of the Cat Allergen Fel d1 from House Dust with a Swab Analyzer According to the Present Invention a) Preparation of the Gold Marker 0.5 L of distilled and filtered (0.2 μm) water was heated to a boil while stirring in a siliconized beaker and 5 mL of 1% auric acid were added. The solution was boiled for another 5 minutes and 20 mL of 1% sodium citrate solution were then rapidly added. A change in color from blue to red after another 10 minutes indicated the end of the reaction. The colloid was cooled to room temperature in an ice bath and stabilized by adding 5 mL of 2% $NaN_3$ solution and 0.5 mL of 1% PEG (polyethylene glycol) 20000.

b) Preparation of the Gold Marker Conjugate

The pH value of the gold colloid solution was adjusted to pH 9 by adding 0.2 M of $K_2CO_3$. Ten mg of this first monoclonal antibody specific of Fel d1 were added to the solution and incubated for 30 minutes at room temperature. After adding 200 mg of bovine serum albumin to the solution and incubation for another 30 minutes, the conjugates of antibodies and gold markers were obtained by centrifuging for 15 minutes at 40,000 g by taking up the pellet in 0.1 M HEPES (hydroxyethylpiperazineethanesulfonic acid) buffer with pH 7.0, with the addition of 0.1% bovine serum albumin and 0.05% of PEG 20000.

c) Preparation of the Conjugate Mat (Conjugate Zone 5)

F075-14 glass fiber mat material (Whatman, Great Britain) was cut into strips with a width of 0.5 cm and a length of 2.5 cm, impregnated in the gold marker conjugate solution (optical density at 520 nm set at 3) and dried at 40° C. for 20 minutes in a forced-air oven.

d) Preparation of the Reaction Zone 6

A nitrocellulose membrane with a pore size of 5 μm (Schleicher & Schüll, Germany), which had a width of 0.5 cm and a length of 2.5 cm, was fixed as the reaction zone 6 on a plastic laminate 8 with a thickness of 1 mm by means of a two-sided adhesive tape. Using a Camag Linomat IV (Camag, Switzerland), a second monoclonal antibody specific of Fel d1 was sprayed on at a concentration of 1 mg/mL as a linear signal zone 7 (1 μL/cm) 1 cm from the top edge of the nitrocellulose, and an antibody specific of mouse antibody was sprayed on linearly at a distance of 1.5 cm from the edge. The membrane was subsequently dried for 30 minutes at 40° C. in a forced-air oven, blocked for 10 minutes with 0.1% bovine serum albumin solution and dried again for 30 minutes at 40° C.

e) Assembly of the Swab Analyzer

The conjugate mat impregnated with gold marker conjugate (conjugate zone 5) was fixed with a two-sided adhesive tape on the plastic laminate 8 such that it overlapped the reaction zone 6 with its front end by 2 mm. A glass fiber mat GF/F (Whatman, Great Britain) with a length of 2 cm and a width of 0.5 mm, which was used as an absorption mat (collection zone 9), was likewise fixed with a 2-mm overlap at the rear end of the reaction zone 6. A test strip with a width of 0.5 cm, comprising an absorption mat with a length of 2.5 cm (collection zone 9) and, adjoining it, a reaction zone 6 with a length of 2.5 cm and a transfer zone 5 with a length of 2 cm, whose individual components were in capillary transport with one another, was thus obtained. The swabbing pen 2 (diameter 4 mm), which had a height of 7 mm and consisted of sintered polyethylene with a pore size of 70 μm, contacted the test strip at the site of the transfer zone 4. The closed housing 1 of the swab analyzer holds the two components, namely, the swabbing pen 2 and the test strip, in press fit.

f) Preparation of a Model Surface and Sampling of House Dust

Using a laboratory spatula, about 10 mg of fine dust of a 110-μm particle-screened house dust sample were distributed on the surface of five layers (simulation of a soft textile surface) of dust-free very clean room paper towels from the firm of Clear-Clean. According to the Microtiter Plate ELISA, the concentration of cat allergen in the house dust sample is >10 μg of Fel d1/g of house dust.

The swab analyzer was grasped with the hand and, directed downward with the swabbing pen 2, it was swabbed over the distributed dust for 1 minute. The dust penetrates superficially into the pores of the swabbing pen 2. After sampling, the color of the swabbing pen 2 turns gray as a consequence of the enrichment of the particles.

g) Elution of the Cat Allergen Fel d1 and Analysis

Using a 5-mL dropper, 5 drops of an elution liquid were applied to the accurate location of the swabbing pen 2 within 30 seconds. The elution liquid consisted of 0.01-molar sodium phosphate buffer with pH 7.6 with 1% of bovine serum albumin and 0.2% of Tween 20.

h) Evaluation of the Swab Analyzer

Two red lines (signal zone 7) became visible after about 5 minutes. Only a change in the color of the control band took place in the unloaded control samples.

EXAMPLE 2

Detection of Amphetamine Sulfate from Human Saliva with a Swab Analyzer According to the Present Invention a) Preparation of the Gold Marker 0.5 L of distilled and filtered (0.2 μm) water was heated to a boil while stirring in a siliconized beaker and 5 mL of 1% auric acid were added. The solution was boiled for another 5 minutes and 20 mL of 1% sodium citrate solution were then rapidly added. A change in color from blue to red after another 10 minutes indicated the end of the reaction. The colloid was cooled to room temperature in an ice bath and stabilized by adding 5 mL of a 2% $NaN_3$ solution and of 0.5 mL of 1% PEG (polyethylene glycol) 20000.

b) Preparation of the Gold Marker Conjugate

The pH value of the gold colloid solution was adjusted to pH 9 by adding 0.2 M of $K_2CO_3$. Ten mg of a first amphetamine-specific monoclonal antibody were added to the solution and incubated for 30 minutes at room temperature. After adding 200 mg of bovine serum albumin to the solution and incubation for another 30 minutes, the conjugates of antibodies and gold markers were obtained by centrifuging for 15 minutes at 40,000 g by taking up the pellet in 0.1-M HEPES (hydroxyethylpiperazineethanesulfonic acid) buffer with pH 7.0, with the addition of 0.1% of bovine serum albumin and 0.05% of PEG 20000.

c) Preparation of the Conjugate Mat (Conjugate Zone 5)

F075-14 glass fiber mat material (Whatman, Great Britain) was cut into strips with a width of 0.5 cm and a length of 2.5 cm, impregnated in the gold marker conjugate solution (optical density at 520 nm set at 3) and dried at 40° C. for 20 minutes in a forced-air oven.

d) Preparation of the Reaction Zone 6

A nitrocellulose membrane with a pore size of 5 μm (Schleicher & Schüll, Germany), which had a width of 0.5 cm and a length of 2.5 cm, was fixed as the reaction zone 6 on a plastic laminate 8 with a thickness of 1 mm by means of a two-sided adhesive tape. Using a Camag Linomat IV (Camag, Switzerland), an amphetamine polyhapten was sprayed on at a concentration of 1 mg/mL as a linear signal zone 7 (1 μL/cm) 1 cm from the front edge of the nitrocellulose, and a mouse antibody-specific antibody was sprayed on linearly at a distance of 1.5 cm from the edge. The membrane was subsequently dried at 40° C. for 30 minutes in a forced-air oven, blocked for 10 minutes with a 0.1% bovine serum albumin solution, and dried again for 30 minutes at 40° C.

e) Assembly of the Swab Analyzer

The conjugate mat impregnated with gold marker conjugate (conjugate zone 5) was fixed on the plastic laminate 8 with a two-sided adhesive tape such that it overlapped the reaction zone 6 at its front end by 2 mm. A glass fiber mat GF/F (Whatman, Great Britain) with a length of 2 cm and a width of 0.5 cm, which was used as an absorption mat (collection zone 9), was fixed likewise with a 2-mm overlap at the rear end of the reaction zone 6. A test strip with a width of 0.5 mm, comprising an absorption mat with a length of 2.5 cm (collection zone 9) and, adjoining it, a reaction zone 6 with a length of 2.5 cm and a transfer zone 4 with a length of 2 cm, whose individual components were in capillary transport with one another, was thus obtained. The cylindrical swabbing pen 2 (diameter 4 mm), which had a height of 7 mm and consisted of sintered polyethylene with a pore size of 70 μm, contacted the test strip at the site of the transfer zone 4. The closed housing 1 of the swab analyzer holds the two components, namely, the swabbing pen 2 and the test strip, in press fit.

f) Saliva Sampling

One mL of human saliva was sampled and mixed with 100 ng of amphetamine. The positive sample thus obtained was applied to a bovine tongue by means of a brush. The swab analyzer was grasped by the hand and, with the swabbing pen 2 directed downward, it was passed over the tongue once.

g) Elution of the Amphetamine and Analysis

Using a 5-mL dropper, 5 drops of an elution liquid were applied within 30 seconds to the accurate location of the swabbing pen 2. The elution liquid consisted of 0.01-molar sodium phosphate buffer with pH 7.6 with 1% of bovine serum albumin and 0.2% of Tween 20.

h) Evaluation of the Swab Analyzer

A red line (signal zone 7) became visible after about 5 minutes. Two red lines were obtained in the case of unloaded control samples.

While specific embodiments of the invention have been shown and described in detail to illustrate the application of the principles of the invention, it will be understood that the invention may be embodied otherwise without departing from such principles.

What is claimed is:

1. A swab analyzer for the immunochemical detection of substances, the analyzer comprising:

a housing having an outer surface with a local elevation with a central opening, with an at least partially circular collection groove for receiving excess eluent, a window being provided in said housing at a spaced location from said local elevation;

a swabbing pen defining a sampling and eluent application zone with a porous swabbing portion, said pen being disposed in said central opening and projecting from said housing; and a reaction zone with a signal zone, said reaction zone being disposed at least partially under said window, said sampling and eluent application zone as well as said reaction zone with said signal zone being in capillary fluid connection with one another.

2. The swab analyzer in accordance with claim 1, wherein said local elevation is conical.

3. The swab analyzer in accordance with claim 1, wherein said collection groove runs around said local elevation and is concentric with said local elevation.

4. The swab analyzer in accordance with claim 2, wherein said collection groove runs around said local elevation and is concentric with said local elevation.

5. The swab analyzer in accordance with claim 1, wherein a portion of said porous surface of said swabbing pen projects outward from said housing and is rounded.

6. The swab analyzer in accordance with claim 2, wherein a portion of said porous surface of said swabbing pen projects outward from said housing and is rounded.

7. The swab analyzer in accordance with claim 1, wherein said swabbing pen has a pore size of ranging from 10 μm to 100 μm.

8. The swab analyzer in accordance with claim 1, wherein said swabbing pen consists of a sintered or foamed plastic.

9. The swab analyzer in accordance with claim 8, wherein said swabbing pen consists of sintered polyethylene.

10. The swab analyzer in accordance with claim 1, wherein said housing is opened and consists of a plastic especially polypropylene.

11. The swab analyzer in accordance with claim 2, wherein said swabbing pen consists of a sintered or foamed plastic.

12. The swab analyzer in accordance with claim 11, wherein said swabbing pen consists of sintered polyethylene.

13. The swab analyzer in accordance with claim 2, wherein said housing is opened and consists of a plastic especially polypropylene.

14. A process for the immunochemical detection of substances, the process comprising the steps of:

providing a swab analyzer housing having an outer surface with a local elevation with a central opening, with an at least partially circular collection groove for receiving excess eluent, a window being provided in the housing at a spaced location from the local elevation;

disposing a swabbing pen in the central opening projecting from the housing, the pen defining a sampling and eluent application zone with a porous swabbing portion;

disposing a reaction zone with a signal zone, at least partially under the window;

providing the sampling and eluent application zone as well as the reaction zone with the signal zone in capillary fluid connection with one another;

swabbing a surface with the pen; and applying an elution liquid to the pen subsequent to said step of swabbing.

15. The process in accordance with claim 14, wherein the local elevation is provided as a conical form.

16. Process in accordance with claim 14, wherein the collection groove runs around the local elevation and is concentric with said local elevation.

17. Process in accordance with claim 14, wherein a portion of the porous surface of the swabbing pen projects outward from the housing and is rounded.

18. Process in accordance with claim 14, wherein the swabbing pen has a pore size of ranging from 10 μm to 100 μm.

19. Process in accordance with claim 14, wherein the swabbing pen consists of a sintered or foamed plastic.

20. Process in accordance with claim 19, wherein the swabbing pen consists of sintered polyethylene.

21. An immunochemical substance detection swab analyzer, comprising:
   a housing with an outer surface including a support part surrounding an opening, and a collection groove extending around said support part said surface having a window opening at a spaced location from said protruding support part;
   an eluent application porous swabbing pen having a portion extending out of said housing opening and extending outwardly a distance from said housing outer surface, said eluent application porous swabbing pen being supported by said protruding support part of said housing;
   a reaction part with a signal portion for evaluating the state of said reaction part, a portion of said reaction zone being placed under said window opening, said eluent application zone porous swabbing pen, said reaction part and said signal portion being in capillary fluid connection with one another.

22. A swab analyzer in accordance with claim 21, wherein said protruding support part is conical and is extending outwardly from a side of a housing having said window opening and a portion of said surface surrounding said protruding support part includes an annular collection groove for receiving excess eluent.

23. A swab analyzer in accordance with claim 21, wherein said swabbing pen has a rounded porous surface projecting outward from said housing surface.

24. A swab analyzer in accordance with claim 23, wherein said rounded porous surface has a pore size from 10 μm to 100 μm.

25. A swab analyzer in accordance with claim 23, wherein said swabbing pen consists of one of a sintered or foamed plastic.

26. A swab analyzer in accordance with claim 23, further comprising an elution liquid applied to said eluent application zone porous swabbing pen after said eluent application zone porous swabbing pen is used to swab a surface.

* * * * *